United States Patent [19]
Byler

[11] 4,454,869
[45] Jun. 19, 1984

[54] ARTHRITIS RELIEF SUPPORT PAD

[75] Inventor: William H. Byler, Sarasota, Fla.

[73] Assignee: William H. Byler Revocable Trust, Sarasota, Fla.

[21] Appl. No.: 402,608

[22] Filed: Jul. 28, 1982

[51] Int. Cl.$^3$ ............................................. A61F 5/00
[52] U.S. Cl. ..................................................... 128/69
[58] Field of Search ..................... 128/69, 80 R, 67; 5/327 R, 327 B, 337, 338

[56] References Cited

U.S. PATENT DOCUMENTS

| | | | |
|---|---|---|---|
| 2,521,530 | 9/1950 | McGuffage | 128/69 X |
| 2,554,337 | 5/1951 | Lampert | 128/69 |
| 2,612,158 | 9/1952 | Manley | 128/69 |
| 2,818,854 | 1/1958 | Johnson | 128/69 |
| 4,210,134 | 7/1980 | Okazaki et al. | 128/69 X |

*Primary Examiner*—John D. Yasko
*Attorney, Agent, or Firm*—Pennie & Edmonds

[57] ABSTRACT

A support pad for relief of osteoarthritis of the hip joint, which connects the trochanter to the pelvis. The support pad has cushioning means for comfortable placement against the user's pelvis. The cushion has sufficient thickness so that when the user is lying on his side, it shifts body weight bearing pressure from the trochanter to the pelvis to reduce pressure on the hip joint, and thereby reduce pain in the joint. The support pad may have adjustable thickness to accommodate the anatomical geometry and weight of different users. A leg cushion may be used between the inner thighs to further reduce pressure in the hip joints.

11 Claims, 7 Drawing Figures

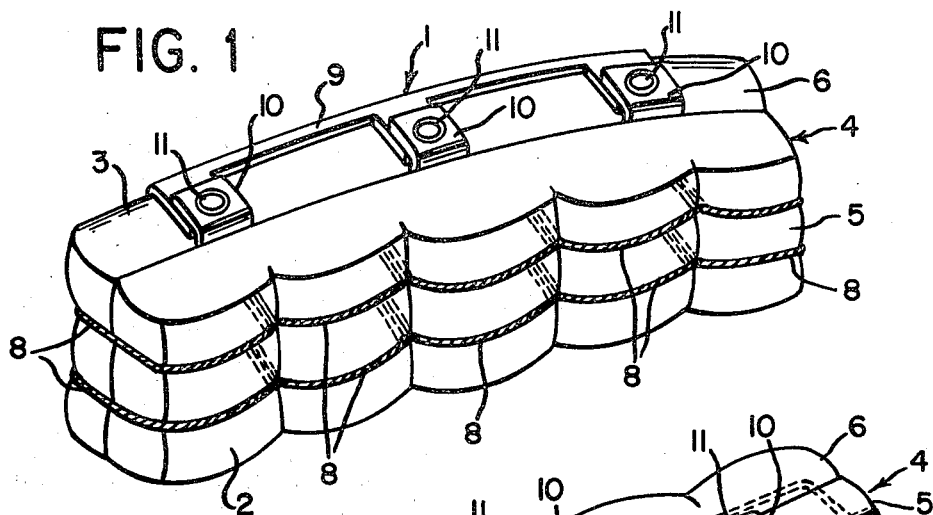
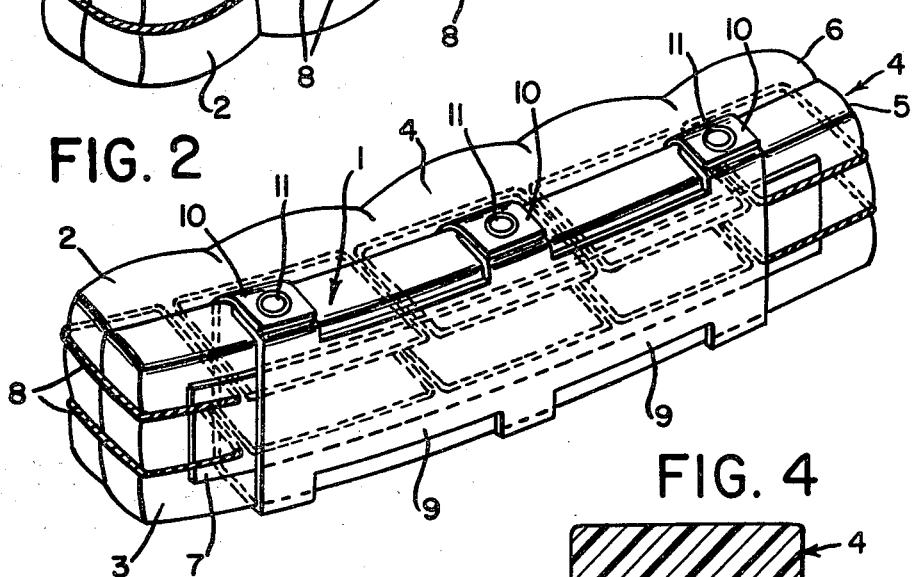
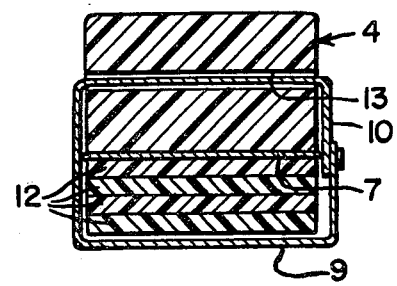
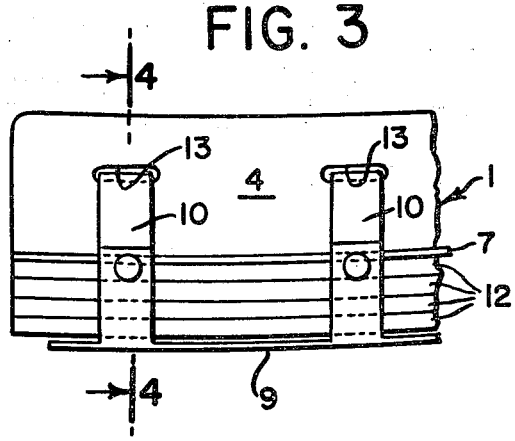

ARTHRITIS RELIEF SUPPORT PAD

BACKGROUND OF THE INVENTION

1. Field of the Invention

This invention relates to a support pad to relieve the pain of osteoarthritis of the hip joint when the disease sufferer lies on his or her side.

2. Description of the Prior Art

Osteoarthritis of the hip joint involves deterioration of cartilage covering the contact surfaces of the ball and socket portions of the joint. In human anatomy, the thigh bone (femur) has a laterally protruding part called the greater trochanter, which extends laterally on the order of one inch further than the lateral protrusion of the pelvis (ilium), the protrusion being called the pelvic crest. The hip joint ball is attached to the trochanter, and the hip joint socket is attached to the pelvis. The hip joint connects the trochanter of the thigh bone to the pelvis.

Deterioration of the cartilage covering the hip joint surfaces causes inflammation and often becomes extremely painful, crippling some sufferers. When lying on one's side in bed, the lateral protrusion of the greater trochanter creates greater pressure on the greater trochanter and the rest of the thigh bone than on the pelvic crest, causing undesirable pressure on the hip joint.

Some sufferers of osteoarthritis experience pain when sleeping because body weight applies pressure on the joint. The joint pain often prevents comfortable sleep.

SUMMARY OF THE INVENTION

I have found that the joint pain experienced while in a reclining position may be alleviated by shifting weight bearing pressure from the thigh bone to the pelvis. In accordance with the teachings of the present invention, this is accomplished by use of a unique support pad. Placement of a support pad between the pelvis and the bed mattress or other body supporting surface on which the individual lies shifts weight bearing pressure from the trochanter to the pelvis, thus decreasing pressure at the joint. Reducing hip joint stress dramatically reduces pain which, in turn, promotes sleeping comfort and joint healing.

The arthritis relief support pad combines cushion means for placement against the pelvis and spacing thickness for lifting the pelvis relative to the supporting surface a distance sufficient to shift weight bearing pressure normally acting on the trochanter to the pelvis. The support pad may have one or more independent stacked spacers attached to the base of the cushion in order to adjust the pad thickness to suit the weight and measurements of different users. The support pad had a base which provides dimensional stability to the pad while having sufficient longitudinal flexibility to allow the pad to conform to body curvature.

In one embodiment, the support pad is a relatively small stationary pad placed between the user's pelvic crest on one side of the body and the bed mattress. This embodiment is suitable for users who move relatively little during the course of their sleep. It must be reset to a proper supportive position if the user turns over during sleep. Antifriction means, such as canvas, may be added to the outer surface of the support pad to allow its slippage on the mattress during placement.

In another embodiment, the device is a belt which girds the user's waist over both the left and right pelvic crests. This embodiment is useful for users who move in their sleep and who want to avoid manual pad placement when they do move.

In either embodiment, a leg cushion inside one of the user's thighs can be used to reduce pressure in both hip joints.

BRIEF DESCRIPTION OF THE DRAWINGS

FIG. 1 is a top perspective view of the support pad;

FIG. 2 is a bottom perspective view of the support pad;

FIG. 3 is an elevational view of a portion of another embodiment of the support pad;

FIG. 4 is an elevational, cross-sectional view of the support pad taken along 4—4 of FIG. 3;

DESCRIPTION OF THE PREFERRED EMBODIMENTS

Figure 5:
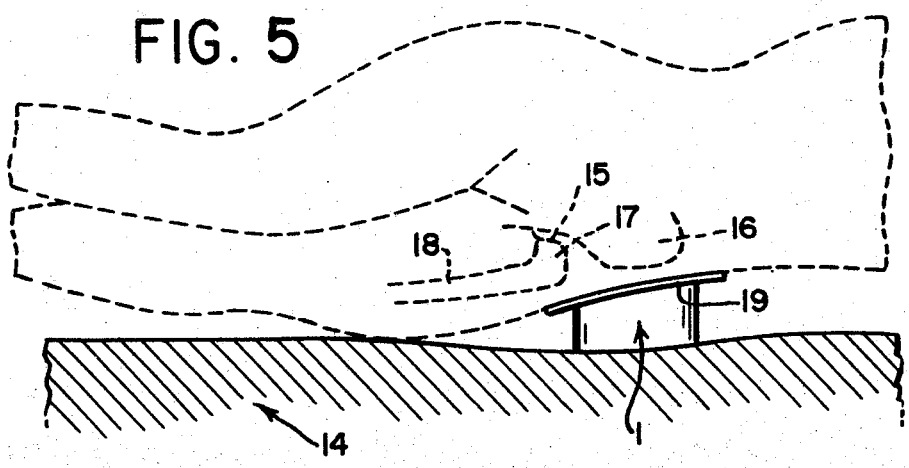
FIG. 5 is a schematic elevational view of the support pad showing its position during use and with the body and bones shown in broken lines.

Support pad 1, shown in FIGS. 1 and 2 has a top surface 2 and a bottom surface 3. These surfaces are in effect the opposite surfaces of a cushion structure 4. The cushion 4 acts as padding against the body of the user when placed against the skin covering his pelvic crest while serving the primary purpose of shifting upward pressure from the trochanter to the pelvis. In the embodiment shown in FIGS. 1 and 2, cushion 4 has two or more layers 5 and 6 of cushion material stacked upon each other. I have found that polyurethane foam is a suitable cushioning material for application in this device, although other types of cushioning material may be used.

A base 7 is shown attached to the bottom surface of the support pad. Base 7 is constructed of a thin, but relatively rigid or stiff material, such as plastic, dense cardboard, such as draftsman's bristol board, or light metal attached to the cushion 4, in order to add structural stability to the otherwise yielding cushion. As shown in FIGS. 1 and 2, base 7 is attached to the cushion 4 by means of tensioned stitched cord loops 8 which run in a longitudinal direction, (i.e., the longest dimension of the device). The cord loops 8 pass through base 7 and the stacked cushion layers 5 and 6.

When the cord 8 is fastened, the tension force compresses cushion 4 along the base 7 and top surface 2. The large surface area of base 7 distributes the tension force along a large area so that the base sinks very little into the bottom surface 3. Since base 7 as shown in FIGS. 1 and 2 does not cover all of the bottom surface 3, the cushion 4 slightly deforms into narrow raised strips along the edges. The edges help to prevent base 7 contact with the user's body.

Cord 8 tension deforms the cushion top surface 2 along the two lines of cord. Cushion material between the lines of cord 8 is compressed more than foam at the edges and thereby creates a trough-shaped lateral cross section. The trough shape aids the user in keeping the pad in proper position over the convex curvature of the pelvic crest. The top surface 2 also deforms in the longitudinal direction along the cord 8. The cushion undergoes greater compression where the cord passes through the cushion due to a relatively high force concentration. The top surface 2 longitudinally deforms to a convex shape between every two points where the cord passes through the cushion and thus creates longitudinal pad curvature. Greater cushion compression near where the cord 8 passes through the cushion 4 also makes the pad readily conform to body curvature. However, the pad may also be constructed with a pre-curved shape by using a rigid, pre-curved base 7.

In use, the cushion 4 may cling to bed sheets, making initial pad positioning more difficult. To ease pad slippage, antifriction means is attached to the support pad's bottom surface 3. The preferred antifriction means is constructed of canvas.

As shown in FIGS. 1 and 2 the canvas antifriction means is a cross piece 9, which abuts base 7 along the support pad bottom surface 3. The cross piece 9 is attached to the support pad 1 by straps 10. The straps 10 pass between the cushion layers 5 and 6 in the width dimension. Straps 10 have fasteners 11 to fasten the strap ends into continuous loops.

Cushion thickness determines the amount of weight bearing pressure that is shifted to the pelvis. Due to individual variations in greater trochanter lateral protrusion, different users require different amounts of cushion thickness to properly transfer pressure from the thigh bone to the pelvis.

To satisfy this need, the support pad, shown in FIGS. 3 and 4, is constructed with one or more independent spacers 12 of known thickness that are stacked under the cushion 4 to effect a desired pad thickness. The spacers 12 are attached to the device by the straps 10 passing through slots 13 in the cushion. It is convenient to construct the straps 10 as integral extensions of the cross piece 9 and to make them long enough to carry rows of fasteners 11 (not shown) so that the integral unit serves as a variable depth pocket for adding spacers 12. With this embodiment, consumers can purchase one common cushion and easily adjust cushion thickness.

The spacers 12 are manufactured of cushion material, such as foam, or a hard, generally rigid material, e.g. wood, plastic or rubber, which resists deformation by body weight application. Rigid spacers may be constructed of a string of individual segments a few inches long held together by flexible members, such as string, so that they easily conform to the desired curvature of the device due to freedom of movement between each individual segment. Alternatively, rigid spacers may be constructed to match the desired curvature of the support pad device.

The support pad 1 is designed for two major forms of use, depending upon the sleeping habits of the user. In the first form, intended for users who do not move very much while sleeping, the short, pad-like device, shown in FIGS. 1-4, is suitable. The user places this device between his pelvic crest and the supporting surface, such as mattress 14. FIG. 5 shows a schematic view of the support pad 1 in use for the hip joint of an arthritic sufferer. Hip joint 15 is the affected joint. As shown, the support pad 1 acts as an extension of the pelvic crest of pelvis 16 and increases body weight bearing distribution on the pelvis while concomitantly transferring weight from the trochanter of thigh bone 18. The pad may also have a lateral extension at approximately right angles (not shown) which contacts the user's gluteus maximus just behind the trochanter 17 and depresses the mattress to reduce pressure on the joint. It is not feasible to use an extension below or in front of the trochanter because it restricts leg movement during sleep.

I have also found that an additional sheet of polyurethane foam pad 19 placed directly upon the skin under night clothing helps prevent irritation which might occur from wrinkles in the clothing if the device is placed over garments during use. A ⅛" to ¼" thick sheet of the polyurethane foam is suitable for this additional padding application.

Figure 6:
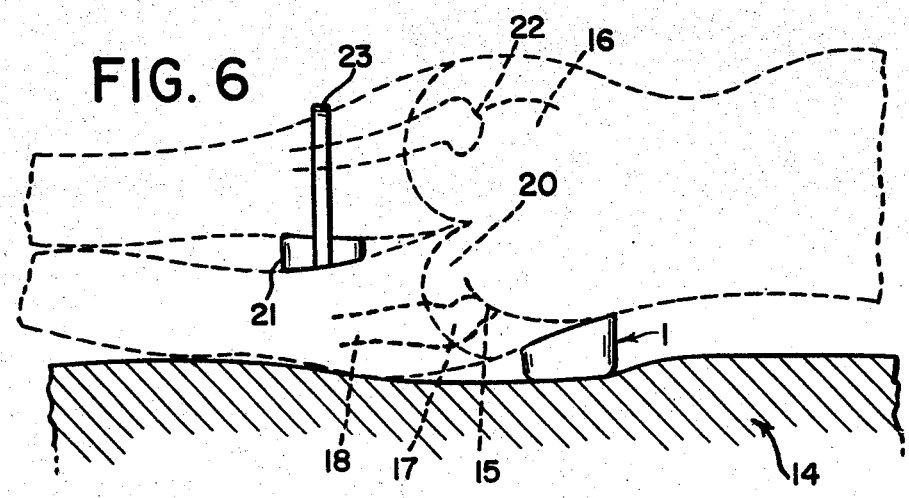
FIG. 6 is a schematic elevational view of one embodiment of the support pad while in use, taken from the posterior of the user.
Figure 7:
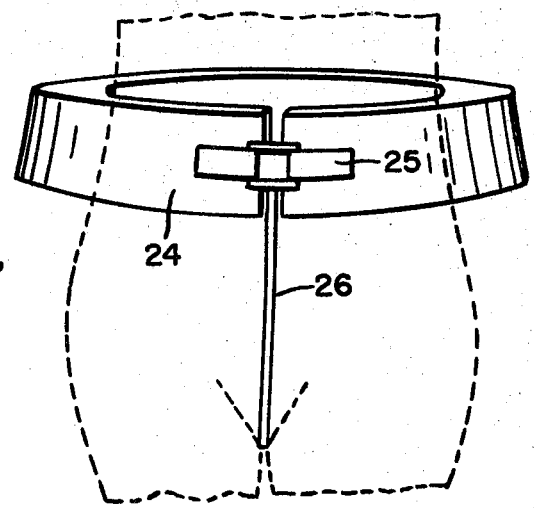
FIG. 7 shows use of still another embodiment of the support pad.

A leg cushion 21 may be used with the support pad to relieve joint pressure and pain from the upper hip joint. When the user is lying on his side, as shown in FIG. 6, the weight of the upper leg presses down on the upper hip joint 22. Placement of the leg cushion 21 between the inner thighs counteracts the gravitational load of the upper leg on the upper hip joint 22. Leg cushion 21 also tends to separate the joint components of the lower hip joint 15, but this is counteracted by pressure of the mattress 14 against the trochanter 17, which compresses the joint components.

I have found that leg cushion 21 thickness of between approximately 4" and 5" reduces the upper hip joint 22 pain. I have also found that width of between 4" and 5" and length of between approximately 8" and 10" works well with a 4" thick pad. A strap or band 23 secures the leg cushion 21 to one of the user's thighs to prevent its movement during sleep or by any user who wants to avoid manual placement of the pad when he changes position. The leg cushion 21 is placed inside or outside the night garments.

The second form of use of the support pad of the present invention is one adapted for use by a user who tends to move around in his sleep or by any user who wants to avoid manual pad placement when he changes sleep position. When this is the case, the support pad is constructed into a belt 24 which extends around the pelvic crests on both the left and right sides of the body. The user straps belt 24 over both crests of his pelvis and tightens it with strap 25. To prevent vertical movement of the belt during sleep, the user may use an optional crotch strap 26.

Construction of the device with certain dimensional characteristics has lead to the most suitable performance results, but it should be understood that variations in these dimensions may be necessary for persons of different anatomical builds. The most suitable dimension for support pad width is between 3" and 5". Three inches is approximately the minimum amount of width necessary to comfortably distribute body weight along the pelvic crest and to secure the lateral position of the pad over the crest. The upper range of width of approximately 5" prevents uncomfortable contact with the rib cage or pad extension under the trochanter. The latter would defeat the pad's purpose.

Cushion thickness is predominantly dictated by comfort to the user. Lighter users may be satisfied with an approximately 2½" thick polyurethane foam cushion, whereas heavier users may require more. Polyurethane cushioning material tends to flatten and loose resiliency after a long period of use. A cushion having an initial thickness of 4" allows for some compression during the support pad's useful life. After compression of the cushion, additional lift is added by the use of spacers 12. Pad length for the short pad is between approximately 12 inches and 15 inches, while the belt embodiment must have sufficient length of wrap around both of the user's pelvic crests.

I claim:

1. An arthritis relief support pad having length, width and thickness dimensions for placement on the pelvic crest of the pelvis of a user lying on his side on a supporting surface to shift body weight bearing pressure from the trochanter to the pelvis and thereby relieve pressure on the hip joint connecting the pelvis and trochanter, the support pad comprising:
   (a) cushion means for cushioning the pelvic crest and for lifting the pelvis relative to the supporting surface a distance sufficient to shift weight bearing pressure normally acting on the trochanter to the pelvis, said cushion having a top surface for placement against the crest of the pelvis and a bottom surface for placement against the supporting surface; and
   (b) a dimensionally stable base attached to the bottom surface of the cushion means.

2. The support pad according to claim 1 wherein:
   (a) the support pad has a curved shape in the length dimension for following the circumferential curvature of the user's hip.

3. The support pad according to claim 1 wherein:
   (a) the pad has a length for wrapping around the user for placement on both pelvic crests.

4. The support pad according to claim 1 wherein:
   (a) the cushion means has two or more layers of cushion material stacked upon each other; and
   (b) two or more loops of cord running through the cushion material in the thickness dimension and along the longitudinal dimension for binding the cushion layers and the base into a unitary support pad.

5. The support pad according to claim 4 wherein:
   (a) the pad has a length of between approximately 12 and 15 inches;
   (b) the pad has a width of between approximately 3 inches and 5 inches; and
   (c) the pad has a thickness of between approximately 2½ inches and 4 inches.

6. An arthritis relief support pad having length, width and thickness dimensions for placement on the pelvic crest of the pelvis of a user lying on his side on a supporting surface to shift body weight bearing pressure from the trochanter to the pelvis and thereby relieve pressure on the hip joint connecting the pelvis and trochanter, the support pad comprising:
   (a) cushion means for cushioning the pelvis crest and for lifting the pelvis relative to the supporting surface a distance sufficient to shift weight bearing pressure normally acting on the trochanter to the pelvis, said cushion having a top surface for placement against the crest of the pelvis and a bottom surface for placement against the supporting surface;
   (b) a dimensionally stable base attached to the bottom surface of the cushion means;
   (c) a leg cushion for placement between the user's inner thighs to reduce pressure between hip joint parts; and
   (d) strap means for attaching the cushion to the user's inner thigh.

7. The support pad according to claim 6 wherein:
   (a) the leg cushion has thickness of between approximately 4 inches and 5 inches, a width of between approximately 4 inches and 5 inches, and length of between approximately 8 inches and 10 inches.

8. The support pad according to any one of claims 6 or 7 further comprising:
   (c) spacing means for creating adjustable support pad thickness to accomodate variations in greater trochanter lateral protrusion and weight among different users having:
      (i) one or more stacked spacers, and
      (ii) retaining means attached to the cushion means for attaching the spacers to the bottom surface of the cushion means.

9. The support pad according to claim 8 wherein:
   (a) the spacers comprise generally rigid material.

10. The support pad according to any one of claims 1-5 further comprising:
    (c) spacing means for creating adjustable support pad thickness to accomodate variations in greater trochanter lateral protrusion and weight among different users having:
       (i) one or more stacked spacers, and
       (ii) retaining means attached to the cushion means for attaching the spacers to the bottom surface of the cushion means.

11. The support pad according to claim 10 wherein:
    (a) the spacers comprise generally rigid material.

* * * * *